(12) United States Patent
Tsimafeyeu

(10) Patent No.: US 8,487,083 B2
(45) Date of Patent: Jul. 16, 2013

(54) MONOCLONAL ANTIBODIES CAPABLE OF SIMULTANEOUSLY BINDING DOMAINS II AND IIIC OF TYPE 1 FIBROBLAST GROWTH FACTOR RECEPTOR

(75) Inventor: Ilya Valer'evich Tsimafeyeu, Moscow (RU)

(73) Assignee: OOO "Oncomax", Moscow (RU)

( * ) Notice: Subject to any disclaimer, the term of this patent is extended or adjusted under 35 U.S.C. 154(b) by 0 days.

(21) Appl. No.: 13/261,076

(22) PCT Filed: Jun. 30, 2009

(86) PCT No.: PCT/EA2009/000004
§ 371 (c)(1),
(2), (4) Date: Dec. 12, 2011

(87) PCT Pub. No.: WO2011/000384
PCT Pub. Date: Jan. 6, 2011

(65) Prior Publication Data
US 2012/0141495 A1    Jun. 7, 2012

(51) Int. Cl.
*C07K 16/00* (2006.01)
*C12P 21/08* (2006.01)

(52) U.S. Cl.
USPC ............... 530/388.22; 530/387.1; 530/388.1; 530/388.15

(58) Field of Classification Search
None
See application file for complete search history.

(56) References Cited

U.S. PATENT DOCUMENTS
8,101,721 B2 * 1/2012 Yayon et al. ............... 530/387.1
2005/0147612 A1    7/2005 Yayon et al.

FOREIGN PATENT DOCUMENTS
WO    WO9410202    5/1994

OTHER PUBLICATIONS

Schlessinger J, et al. Molecular Cell, 6:743-750, Sep. 2000.*
Kwabi-Addo B, et al. Endocrine-Related Cancer, 11:709-724, 2004 (only Abstract provided).*
Yiangou C. et al. "Down regulation of a novel form of fibroblast growth factor receptor . . ." British Journal of Cancer 1997.
Siffroi-Fernandez S. et al. "Acidic fibroplast growth factor (FGF-1) and FGF receptor 1 signaling in human Y79 retinoblastoma" Arch Ophthalmol. Mar. 2005 in PubMed.
Yi W. Chen et al. "Basic fibroplast growth factor and fibroblast growth factor receptor-i in human meningiomas" J.Huazhong Univ Sci Tech Med Sci. 2005 25(I).

* cited by examiner

*Primary Examiner* — Robert Landsman
(74) *Attorney, Agent, or Firm* — Aleksandr Smushkovich

(57) ABSTRACT

The invention pertains to the field of medicine, particularly to methods for suppressing the growth of tumors, which comprise blocking the pathological pathway of human fibroblast growth factor/receptor 1 (domains II and IIIc), and for diagnosing malignant neoplasms leading to an excessive proliferation of tumor cells and to the formation of new vessels accompanied by the growth of primary tumors and metastases. This pathway also represents an independent mechanism of tumor resistance to preparations acting on other pathological pathways. Blocking the aforementioned pathway using various substances that neutralize the receptor by bonding only with domains II and IIIc thereof results in the interruption or slow-down of tumor growth. This receptor can also be used as a target for delivery of diagnostic agents being largely present in tumor cells. The invention enables developing new agents for diagnosing and treating diseases related to excessive proliferation and neovascularization.

13 Claims, 9 Drawing Sheets

SEQ ID NO: 1
gataacaccaaaccaaaccgtatgcccgtagctccatattggacatccccagaaa
agatggaaaagaaattgcatgcagtgccggctgccaagacagtgaagttcaaat
gcccttccagtgggaccccaaaccccacactgcgctggttgaaaaatggcaaag
aattcaaacctgaccacagaattggaggctacaaggtccgttatgccacctggag
catcataatggactctgtggtgccctctgacaagggcaactacacctgcattgtgg
agaatgagtacggcagcatcaaccacacataccagctggatgtcgtggagcggt
ccccctcaccggcccatcctgcaagcagggttgcccgccaacaagacagtggccc
tgggtagcaacgtggagt
tcatgtgtaaggtgtacagtgacccgcagccgcatatccagtggctaaagcacat
cgaggtgaacgggagcaagattggcccagacaacctgccttatgtccagatcct
gaagactgctggagttaataccaccgacaaagagatggaggtgcttcacttaaga
aatgtctcctttgaggacgcaggggagtatacgtgcttggcgggtaactctatcgg
actctcccatcactctgcatggttgaccgttctggaagccctggaagagagg

FIG.2

Differences in the expression of FGFR1 between human renal cancer cell lines (Caki-1) and prostate cancer (Du145), and Western blotting analysis (on 3 levels for each line).

MONOCLONAL ANTIBODIES CAPABLE OF SIMULTANEOUSLY BINDING DOMAINS II AND IIIC OF TYPE 1 FIBROBLAST GROWTH FACTOR RECEPTOR

CROSS-REFERENCE TO RELATED APPLICATIONS

This application is a U.S. national stage application of a PCT application PCT-EA2009-000004 filed on 30 Jun. 2009, published as WO/2011/000384, whose disclosure is incorporated herein in its entirety by reference.

FIELD OF THE INVENTION

The invention pertains to the field of medicine and relates to a method for suppressing the growth of tumors, based on blocking the pathway of "human fibroblast growth factor/human fibroblast growth factor receptor 1 (domains II and IIIc)", and to a method for diagnosing malignant neoplasms.

BACKGROUND OF THE INVENTION

This pathological pathway leads to an excessive proliferation of tumor cells and to the formation of new vessels accompanied by the growth of primary tumors and metastases. This pathway also represents an independent mechanism of tumor resistance to preparations acting on other pathological pathways. Blocking the pathway of "fibroblast growth factor/fibroblast growth factor receptor 1" using various substances that neutralize the receptor by bonding only with domains II and IIIc thereof results in the interruption or slow-down of tumor growth. This receptor can also be used as a target for the targeted delivery of diagnostic agents as it is present in large amounts in the cells of numerous tumors.

BRIEF DESCRIPTION OF DRAWINGS AND SEQUENCE LISTING

Figure 1:
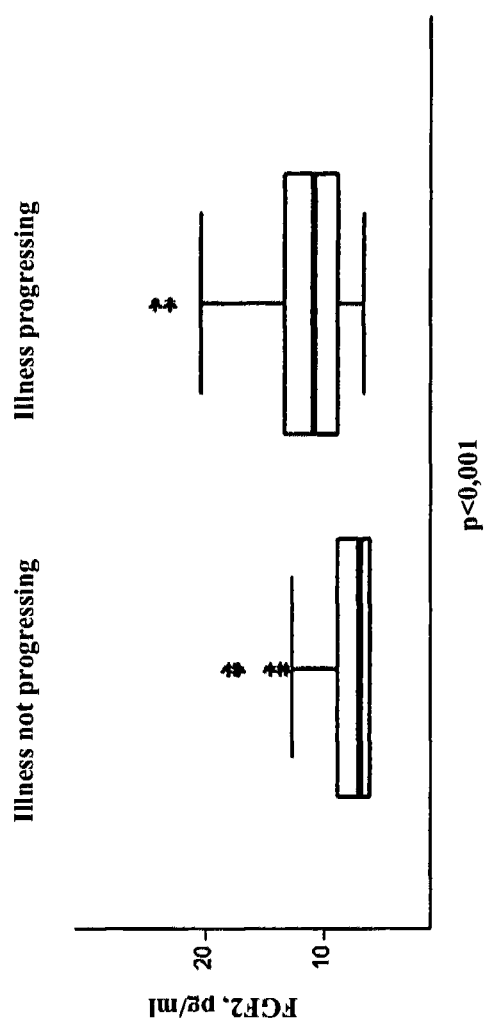

FIG. 1. Difference in concentration of FGF2 in patients with metastatic RCC with the illness progressing and with clinical effect during treatment by target preparations.

FIG. 2. Nucleotide sequence FGFR1 (domains II and IIIc), also recorded as SEQ ID NO: 1 on a compact disc, which nucleotide sequence is hereby incorporated into the instant disclosure. The compact disc contains a file named "Sequence_Listing.txt" created on May 14, 2013 having a size of 1.38 KB.

Figure 3:

FIG. 3. Differences in the expression of FGFR1 between human renal cancer cell lines (Caki-1) and prostate cancer (Du145). and Western blotting analysis (on 3 levels for each line).

Figure 4:
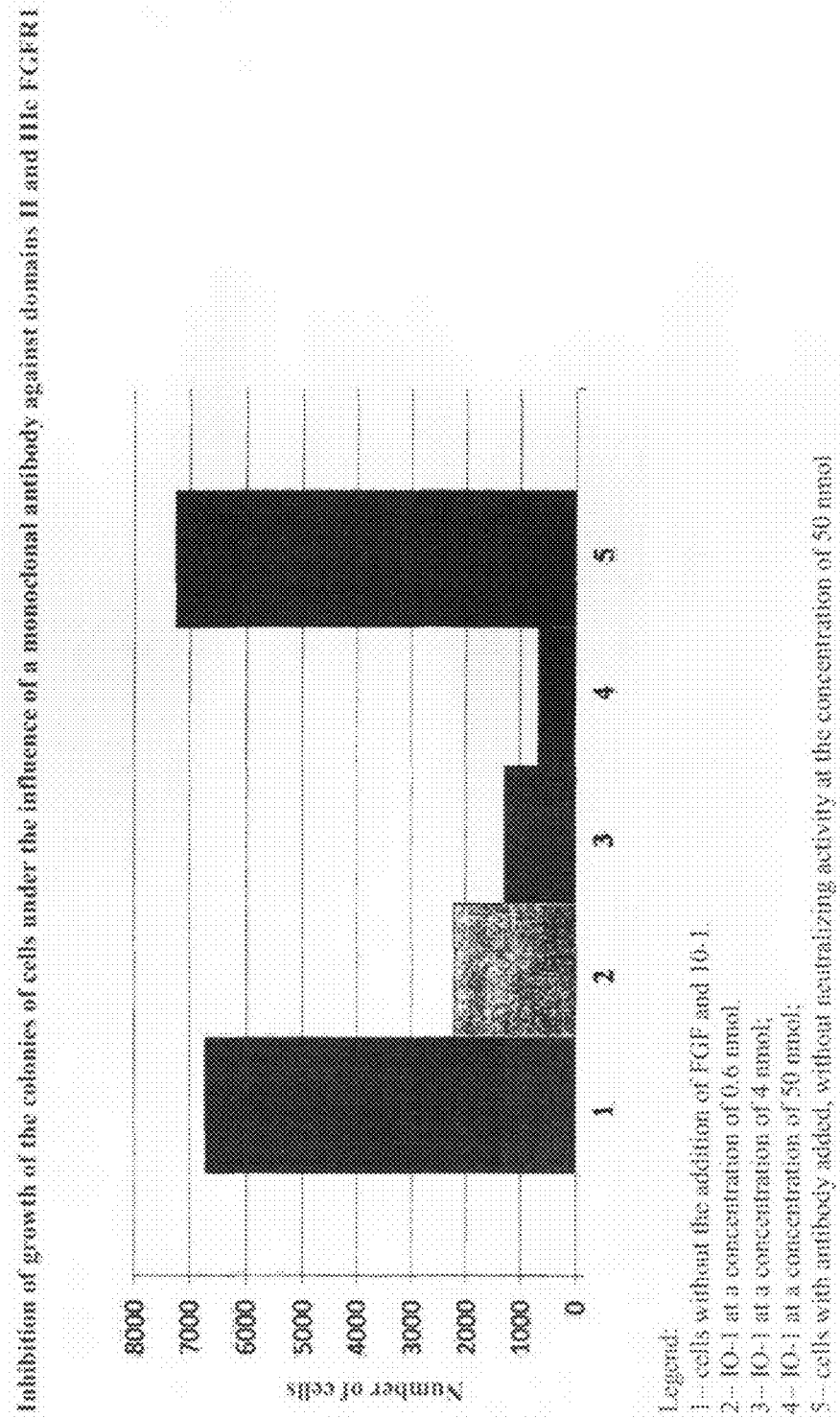

FIG. 4. Inhibition of growth of the colonies of cells under the influence of a monoclonal antibody against domains II and IIIc FGFR1.
Legend:
1—cells without the addition of FGF and 10-1.
2—IO-1 at a concentration of 0.6 nmol.
3—IO-1 at a concentration of 4 nmol;
4—IO-1 at a concentration of 50 nmol;
5—cells with antibody added, without neutralizing activity at the concentration of 50 nmol.

Figure 5:
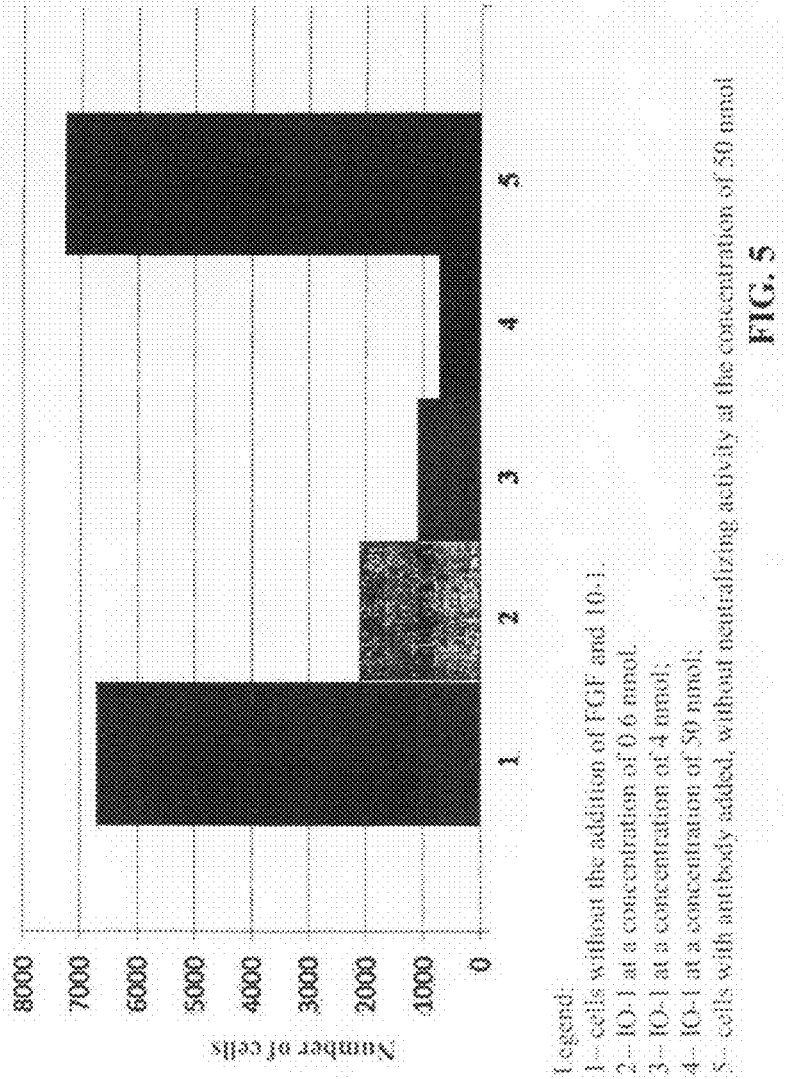

FIG. 5. Inhibition of growth under the influence of cell colonies, under the impact of monoclonal antibody against, because of the FGFR1 sulphate is heparan-sulphate.
Legend:
1—cells without the addition of FGF and 10-1.
2—IO-1 at a concentration of 0.6 nmol.
3—IO-1 at a concentration of 4 nmol;
4—IO-1 at a concentration of 50 nmol;
5—cells with antibody added, without neutralizing activity at the concentration of 50 nmol FIG. 6. Blocking autophosphorylation FGFR1
Legend:
8—cell with FGF and antibodies;
9—cell with FGF added, without antibodies;
10—cell with FGF added, and concentration on antibody (Santa Cruz Biotechnology);
11—cell with $FGF_H$ IO-1 and concentration on at 50 nmol;
12—cell with $FGF_H$ IO-1 and concentration on at 20 nmol;
13—cell with $FGF_H$ IO-1 and concentration on at 4 nmol;
14—cell with $FGF_H$ IO- and concentration on at 2 nmol;
8—cell with $FGF_H$ IO-1 and concentration on at 0.6 nmol.

Figure 7:
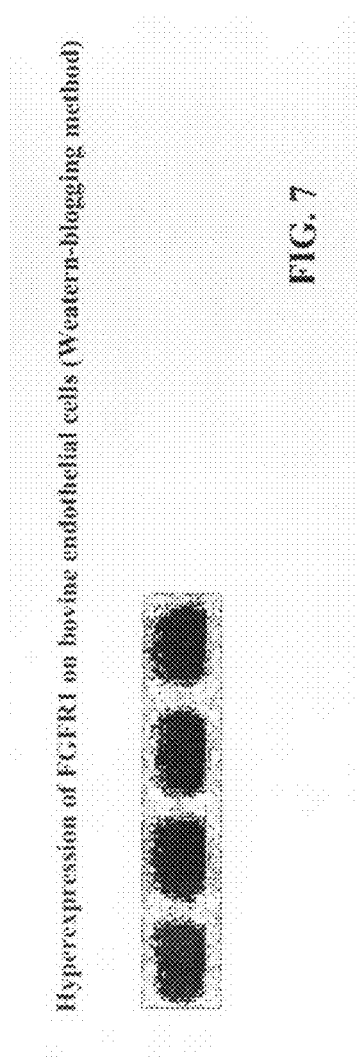

FIG. 7. Hyperexpression of FGFR1 on bovine endothelial cells (Weatern-blogging method)

Figure 8:
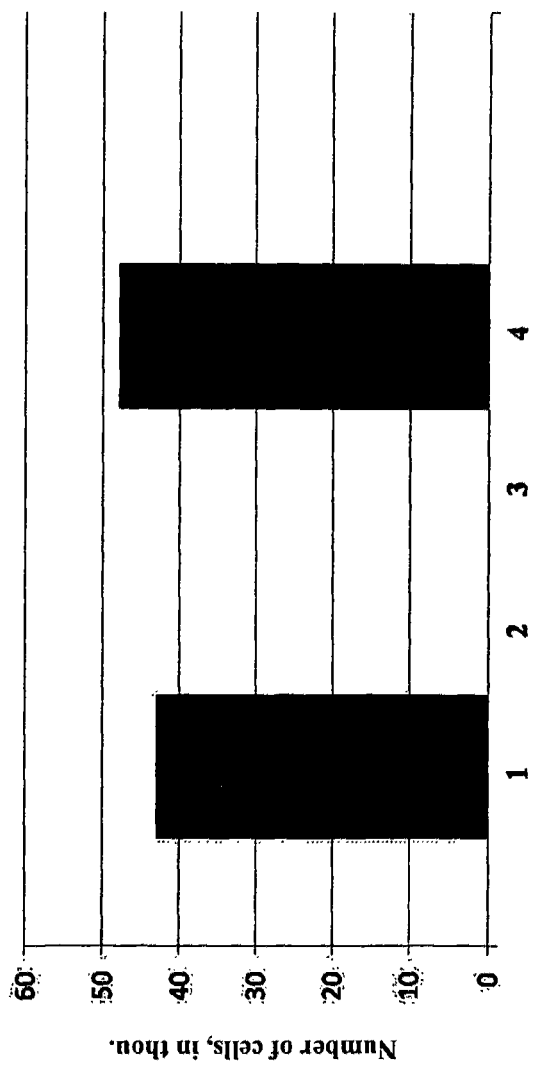

FIG. 8. Inhibition of growth under the influence of cell colonies, under the impact of monoclonal antibodies ($IO-1_H$ IO-2).
Legend:
5—cells without added FGF and antibodies;
6—IO-2 in concentration of 50 nmol: mitogenic activity lower by 97.4%
7—IO-1 in concentration of 50 nmol: mitogenic activity lower by 95.8%
8—cells with added antibodies without the neutralizing activity, at a concentration of 50 nmol.

Figure 9:
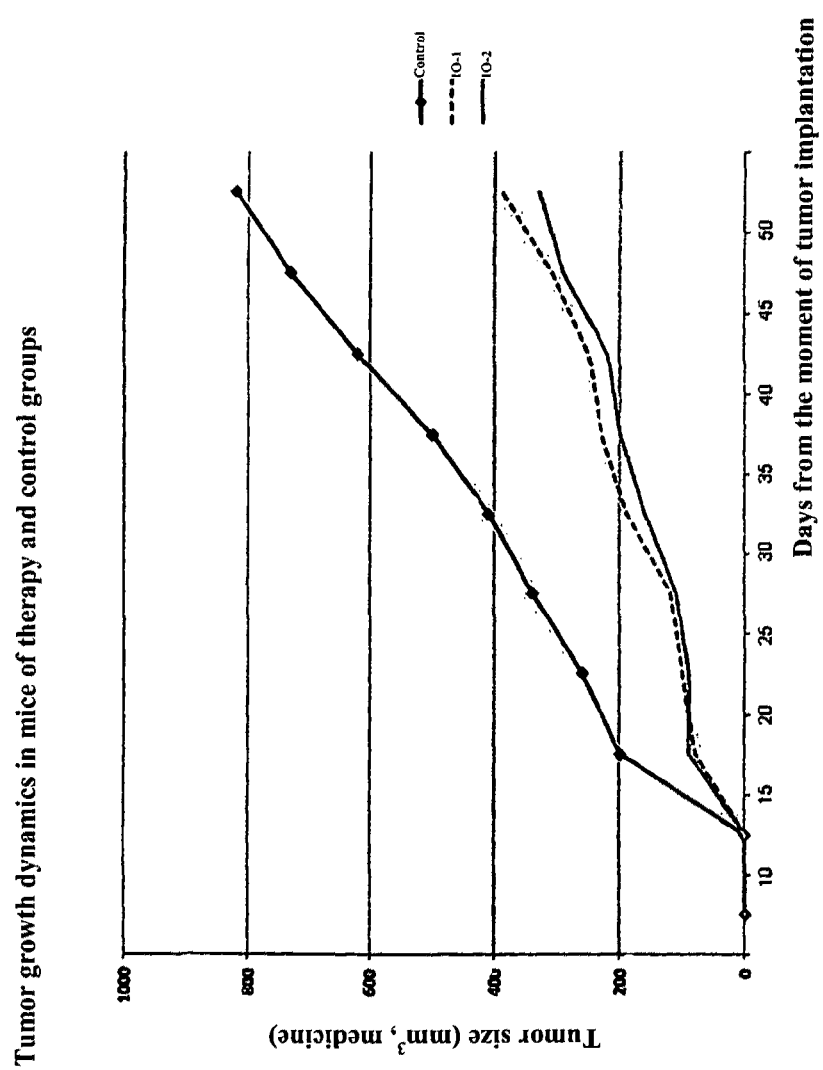

FIG. 9. Tumor growth dynamics in mice of therapy and control groups.

DESCRIPTION OF THE INVENTION

The invention is advantageous in that it makes it possible to develop new agents for diagnosing and treating diseases related to excessive proliferation and neovascularization.

It is known that the basis for the development of malignant neoplasms is excessive cell proliferation and blood vessel formation in a tumor, which is feeding it (angiogenesis). The formation of new blood vessels uses the material from already existing endothelium and is an important component of many diseases and disorders, including such as tumor growth and metastasis, rheumatoid arthritis, psoriasis, atherosclerosis, diabetic retinopathy, retrolental fibroplasia, neovascular glaucoma, hemangiomas, immune rejection of transplanted cornea and other tissues, and chronic inflammations.

In the case of tumor growth, angiogenesis is particularly important during the transition from hyperplasia to neoplasia, as well as to supply feeding to the growing solid tumor (J. Folkman et al. Nature; 339, 58 (1989). Angiogenesis also allows tumors to keep in contact with the host circulatory system, thereby determining the direction of metastasis for tumor cells. Evidence of the role of angiogenesis in metastasis of tumor cells was obtained, in particular, as a result of studies showing the relationship between the quantity and density of microvessels in invasive breast cancer and the actual existence of distant metastases (N. Weidner et al. New Eng. J. Med., 324: 1 (1991).

According to numerous data available proliferation of tumor cells, as well as endothelial cells may be caused by various polypeptides which occur naturally in nature. One of those is the family of fibroblast growth factors (FGF). FGF was initially detected in extracts of the pituitary gland in 1973 (H. Armelin. PNAS 70, 9 (1973).

FGF belong to a family of heparin-binding polypeptides, modulating the function of various cells. FGF have a strong influence on the proliferation and differentiation of tumor and endothelial cells. Currently, 23 members of the FGF family are known (FGF 1-23). Each family member have their own specific functional features. The most well-researched are FGF type 1 and 2 (acidic and basic). In order to have an impact on cells, FGF must bind with a receptor on its surface. There are four types of FGF receptors (FRFR 1-4). FRFR1 binds not only with FGF 1 and 2, but most other members of this family, so the role of this receptor in the conduct of the signal into the cell is considered the most significant.

FRFR1 consists of extramembranous, intramembranous and intracellular parts. The extramembranous part of the receptor consists of three domains (D similar to immunoglobulin. FGF usually interact with the D II and III; heparan sulfate involved in formation of the FRF/FRFR1 complex, interacts with the D III. The alternative mRNA splicing contributes to the formation of several different FRFR1 variants on the cell surface (D Johnson, L. Williams. J Adv. Cancer Res., 60, 1 (1993); McKeehan et al. J Prog Nucleic Acid Res. Mol. Biol., 59, 135 (1998). The intracellular part of the receptor is represented by tyrosine kinases, the autophosphorylation of which results in the further conducting of the signal to the nucleus and the division of the cell.

Research Bureau for the Study of Renal Cancer

Studying the effects of a randomized trial of low molecular weight heparin (LMWH) in patients with metastatic renal cell carcinoma (RCC), we have proved that heparin does have impact on patient survival and on the response rate to immunotherapy. We hypothesized that LMWH can bind FGF, interact with its receptor (FGFR1), other heparan/heparin-binding factors (I. Tsimafeyeu et al. Rossiyskiy Oncologicheskiy Zhournal (Russian Journal of Oncology), No 5 (2008); I. Tsimafeyeu et al. J. Clin. Oncology 25, 18S (2007). In another study, we showed that in 40% of cases patients with metastatic RCC have hemostatic system disorders, which can also be caused by increased formation of FGF and expression of FGFR1 (I. Tsimafeyeu et al. J. Experimental & Clinical Cancer Research, 28, 30 (2009).

In our further studies of the KCRB-L01 and KCRB-L02 we have studied the value of the FGF/FGFR1 complex in the development of RCC.

KCRB-L01. Study of expression of FGFR in patients with RCC. Immunohistochemical studies were performed on sections from paraffin blocks of tumors of 140 patients with RCC. The results were compared with the expression of FGFR in 40 healthy donors who had previously had renal biopsy performed for various reasons without the subsequent discovery of diseases of the organ.

We found expression of FGFR1 in 98% of cases on the cells in the primary renal tumor and in 82.5% of cases in the cells of metastatic RCC. In all cases, the intensity of staining in immunohistochemical analysis was high (3+), which testifies to strong expression of the receptor. In 68% nuclear staining was obtained. FGFR1 expression in cells of healthy renal tissue was found in 1 case (2.5%) due to the staining of blood vessels. Thus, this study confirmed the hypothesis about the appearance and high expression of FGFR1 both on cells of the primary RCC tumor and in metastases (I. Tsimafeyeu et al. ESMO-ECCO 09 (2009): Table 1.

In the study of KCRB-L02, we determined the concentration of FGF 1 and 2, as major factors having mitogenic activity in binding to FGFR1, in the blood plasma of 38 patients with metastatic RCC prior to the targeted therapy, with the disease progressing in the targeted therapy, as well as in blood plasma of 38 healthy volunteers (by the ELISA method). We found that in the blood of healthy people, levels of both FGFs were significantly lower as compared to patients with metastatic RCC (Table 2). The greatest differences were demonstrated for FGF2 ($p<0.001$). With the disease progressing in the targeted therapies (sunitinib, sorafenib) there occurred a significant increase in FGF 2—more than 50% ($p<0.001$), and of FGF-1 by more than 30% ($p<0.05$) as compared to baseline FGF level. When the targeted therapy was effective, no significant change of level of both FGFs was observed ($p=0.3$). The median concentration of FGF 2 in the plasma of patients with and without disease progression, differed significantly ($p<0.001$, FIG. 1). In addition, this study analyzed the level of target for sunitinib/sorafenib—the vascular endothelial growth factor (VEGF).

No statistical differences in the concentration of VEGF in the plasma of patients with RCC in case of progression of the disease and with treatment baseline of ($p=0.2$), as well as correlation with both FGFs ($p>0.1$) were reported.

Thus, the results of the studies for KCRB-L01 and KCRB-L02 suggest that the pathological path of FGF/FGFR1 is not only independent of the development of RCC, but may determine the stability of the existing targeted therapy of tumors. Other authors have also shown the value of FGF/FGFR1 in cases of development of such tumors as non small cell lung cancer, breast cancer, gastric cancer and esophageal cancer, prostate cancer, bladder cancer, head and neck tumors, melanoma (C. Behrens et al. J Clinical cancer research 14, 19 (2008); M. Koziczak et al. J Oncogene, 23, 20 (2004); K. Freier J Oral Oncology 43, 1 (2007); E. Shin et al. J Cancer Res Clin Oncol. 126, 9 (2000); K. Sugiura et al. J Oncology reports 17, 3 (2007); E. Devilard et al. J BMC Cancer 6, 272 (2006); G. Lefevre et al. J Investigative Ophthalmology and Visual Science 50 (2009).

Based on the above, we hypothesized that blocking the FGF/FGFR1 path may cause a disturbance in tumor cell proliferation and an inhibition of angiogenesis. Antagonists of FGFR1, including human monoclonal antibodies, can be used to suppress tumor growth and metastasis.

In addition, the creation of monoclonal conjugates of the antibody (of its fragments) for FGFR1 and contrast agents can be used in the diagnosis of malignant and other neoplasms, whose cells express FGFR1 in large quantities. The aim of the present invention is a method of suppressing tumor growth by blocking (neutralization) of domains II and Inc of FGFR1, as well as a method to diagnose tumors whose cells express FGFR1.

To test the hypothesis and achieve our objectives, we conducted studies of KCRB-L03, KCRB-L04 and KCRB-L05.

In all these studies to block FGFR1 (hereafter FGFR1 refers to a receptor corresponding to registration numbers in international databases Uniprot—PI 1362 and Entrez—2260, namely, its domains II and IIIc (nucleotide sequence which is shown in FIG. 2, SEQ ID NO: 1), while as antagonist substance we used highly specific neutralizing monoclonal antibodies we had synthesized: 1) against the domains FGFR1 II and IIIc (IO-1); and 2) against FGFR1 and heparan sulfate (10-2).

The term "monoclonal antibody" is used here and below to denote an antibody obtained from a population of sufficiently homogeneous antibodies, i.e, individual antibodies comprising a population, identical in their specificity and affinity, except for possible naturally occurring mutations that may be present in minor amounts.

Attention should be paid to the fact that as a result of similar, naturally occurring mutations the content of the monoclonal antibodies of the present invention, which mostly contains antibodies that specifically bind the FGFR1 or the FGFR1/heparan-sulfate complex or the FGF/FGFR1 complexes or inhibit the binding of FGF with FGFR1.

Thus, the term "monoclonal" indicates the character of the antibody originating from the sufficiently homogeneous population of antibodies, which does not mean that the antibodies must be produced in any particular way. For example, monoclonal antibodies described herein can be obtained from hybridoma method (G. Köhler, C. Milstein. J Nature 256, 495 (1975) or with the use of methods that use recombinant DNA (S. Cabilly et al. U.S. Pat. No. 4,816,567).

Upon receipt of monoclonal antibodies by hybridoma, the mouse or other appropriate host animal is immunized with antigen by subcutaneous, intraperitoneal, or intramuscular injection in order to identify lymphocytes that produce or are capable of producing antibodies which specifically bind to the protein(s) used for immunization. Alternatively, lymphocytes may be immunized in vitro. Then the lymphocytes are fused with myeloma cells using an appropriate agent, such as polyethylene glycol, to create a hybridoma cell (J. Goding. Monoclonal Antibodies: Principles and Practice, pp. 59-103 (Academic Press, 1986).

In this invention, such an antigen is FGFR1 (domains II and IIIc) or the FGFR1/heparan-sulfate complex. The antigen may be a fragment or portion of FGFR1, having one or more amino acid residues that are involved in the binding of FGF.

The hybridoma cells thus prepared were seeded and grown in a suitable culture medium that preferably should contain one or more substances that inhibit the growth or survival of the unfused, parental myeloma cells. For example, if the parental myeloma cells do not contain the enzyme hypoxanthineguaninphosphoribosiltransferase (HGPRT or GPRT), the culture medium for the hybridomas typically will include hypoxanthine, aminopterin and thymidine (the HAT medium), the substances that prevent the growth of cells that do not have HGPRT.

It is preferable to choose such myeloma cells that fuse efficiently, support a stable high level expression of antibodies in the selected cells which produce antibodies, and which are sensitive to the media, such as, for example, the HAT medium.

Among such cells the preferred cell lines are mouse myeloma lines, such as lines derived from murine tumors MPC-21 and MPC-11, which can be obtained from the Center for the distribution of cells of Salk Institute, San Diego (Calif., USA), SP-2 cells, which can be obtained from American Type Culture Collection in Rockville (Md., USA) and cells P3X63Ag8U.1, described by Yelton et al (J Curr. Top. Microbiol. Immunol. 81, 1 (1978). In addition, cell lines from human myeloma have been described, and from mouse-human-heteromieloma, capable of producing human monoclonal antibodies (D. Kozbor et al. J Immunol. 133, 3001 (1984); B. Brodeur, P. Tsang Monoclonal Antibody Production Techniques and Applications, pp. 51-63 (Marcel Dekker Inc., New York, 1987).

The cultural medium in which the hybridoma cells are grown, is analyzed for the production of monoclonal antibodies directed against the relevant antigen. The specificity of binding the monoclonal antibodies produced by hybridoma cells should preferably be high. The present invention includes those monoclonal antibodies (10-1/10-2), which showed high specificity (at least 5×109) of binding to these antigens, determined by the standard method of <<BIOCORE>>. In other words, the antibodies bind at least one of these antigens in the analysis of the binding and can inhibit biological activity of the FGFR1. The high specificity and strong blocking of the path are provided due to the simultaneous binding with domains II and IIIc of this receptor.

After determining the hybridoma cells that produce antagonistic antibodies of desired specificity, affinity and activity, the clones may be subcloned by limited dilution and grown by standard methods (J. Goding. Monoclonal Antibodies: Principles and Practice, pp. 59-103 (Academic Press, 1986). Suitable culture media include, for example, the Needle medium, a modified Dulbecco (SIMD), or RPMI-1640 medium. In addition, the hybridoma cells can be grown in vivo in animals as ascites tumors.

Monoclonal antibodies, produced by subclones, are separated from the culture medium, ascites fluid or plasma by using conventional methods of immunoglobulin treatment, such as, for example, protein A-Sepharose, hydroxylapatite chromatography, electrophoresis in gels, dialysis, or affinity chromatography.

DNA encoding the monoclonal antibodies described in the present invention can be readily isolated and sequenced by conventional methods (e.g., using oligonucleotide probes capable of binding specifically to genes encoding the heavy and light cepa of murine antibodies).

As a source of DNA hybridoma cells were used. After being isolated, the DNA may be placed in expression vectors, which are then transfected into host cells such as simian cells of the COS line, Chinese hamster ovary cells (CHO) or myeloma cells that in a different situation do not produce immunoglobulin protein, in order to achieve the synthesis of monoclonal antibodies in the recombinant host cells. DNA can be modified by choice in order to change the nature of the immunoglobulin produced by expression of the DNA.

For example, the humanized forms of mouse antibodies can be obtained by replacing the complementarity determining region (CDR) of the variable domain of a mouse antibody by the corresponding region of a human antibody. In some variants, individual amino acids from the fundamental region (FR) of the mouse antibody are also replaced by the corresponding amino acid residues of human antibodies (P. Carter et al. Proc. Nat. Acad. Sci. 89, 4285 (1992); P. Carter et al. J Biotechnology 10, 163 (1992).

Chimeric forms of murine antibodies can also be obtained by substitution of the homologous murine sequences on the DNA by the sequence encoding a specific area of human immunoglobulin constant chains (heavy and light) (S. Cabilly et al. U.S. Pat. No. 4,816,567; S. Morrison et al. Proc. Nat. Acad. Sci. 81, 6851 (1984). The antibodies used to test the objectives of the present invention include mouse antibodies (IgG).

However, other forms of antibodies can be obtained, "humanized" ones, as well as fully human, which only reflects the percentage of human protein and does not affect the specificity of binding to the antigen, i.e., proof of the method of the present invention.

In addition all the classes of antibodies can be easily obtained for blocking FGFR1 and its domains (e.g., IgA, IgD, IgE, IgG and IgM) and immunoglobulin subclasses, as well as antibody fragments (e.g., Fab, F(ab')2, and Fv), as long as they show the ability to bind FGFR1 and as long as they show antagonism to biological activity of the FGF/FGFR1 path, which is checked in the present invention.

In the case of the preferred variant of this invention monoclonal antibodies will show affinity for the immunizing antigen at a rate of at least 109 liters/mol (P. Munson, D. Rodbard. J Anal. Biochem. 107, 220 (1980).

In addition, monoclonal antibodies will usually inhibit the mitogenic or angiogenic activity of FGFR1 at least 90%, as was determined, for example, in the analysis of cell survival or cell proliferation in vitro, similar to that described in our studies KCRB-L03 (Example 1) and KCRB-L04 (Example 2).

For therapeutic and diagnostic application it is desirable that the monoclonal antibodies reacted not with all the components and molecular forms of FGFR1. For example, it is desirable to obtain a monoclonal antibody that specifically binds only to the domains of FGFR1 II and IIIc, and not to domain I or other domains and isoforms of the receptor. For this the immunization was carried out by the extracellular part of FGFR1, including domains II and IIIc. The required molecular forms of antibodies are easily determined by comparing the ELISA test or by comparing immunopripitation of different polypeptides FGFR1. This makes possible the immunization of different isoforms with FGFR1.

FGFR1 can also be blocked by other known methods, in particular, inhibitors created by chemical synthesis.

The Therapeutic Use of the Process of Blocking the FGF/FGFR1Path.

To use the method described in the present invention in therapeutic practice, FGF/FGFR1 antagonists are introduced to any mammal, preferably a human, in a pharmaceutically acceptable form, including intravenous administration, as well as in the following ways: intramuscular, intraperitoneally, intracerebrospinally, subcutaneously, intraarticular, intrasinovially, intrathecally, orally, locally or by inhalation.

Antagonists can also be administered in the tumor, near the tumor, in the lesion or near the lesion, to ensure local action, along with systemic therapeutic effects. Such forms of administration include pharmaceutically acceptable carriers, which by their nature do not have any toxic or therapeutic effects. Examples of such carriers are ion-exchange material, alum, aluminum stearate, lecithin, plasma proteins (such as human plasma protein), buffer substances such as phosphates, glycine, sorbic acid, potassium sorbate, partial glyceride mixtures of saturated vegetable fatty acids, water, salts or electrolytes, such as protamine sulfate, sodium hydrophosphate, potassium hydrophosphate, sodium chloride, zinc salts, colloidal silica, magnesium trisilicate, polyvinyl pyrrolidone, cellulose base material and polyethylene glycol. Carriers for local or gel-based forms of antagonist include polysaccharides such as sodium carboxymethylcelluloses or methylcelluloses, polyvinylpyrrolidone, polyacrylates, polymers of polioxiethilene polioxipropilene block, polyethylene glycol, and alcohols.

For administration in all cases conventional dosage forms are used, taken from stocks. Such forms include, for example, microcapsules, nanocapsules, liposomes, plasters, inhalation preparations, sprays, sublingual tablets and medicines with constant release of substance. In these preparations the antagonist will usually be present in a concentration of about 0.1 mg/ml to 100 mg/ml.

Suitable examples of drugs with permanent release agents include semipermeable matrices of solid hydrophobic polymers containing the antagonist; such matrices have a definite shape, for example it may be a film or microcapsule. Examples of matrices with constant release include polyethers, hydrogels [e.g., poly(2-hydroxyethyl methacrylate)] as described by Langer et al (J. Biomed. Mater. Res. 15, 167 (1981) and Langer (Chem. Tech. 12 (1982), or poly (vinilalkohol), polylactides (U.S. Pat. No. 3,773,919 N), copolymers of L-glutamic acid and gammaetil-L-glutamate, described by Sidman et al (Biopolymers 22, 547 (1983), undegradable ethylenevinil acetate (Langer et al., see above), the degradable copolymers of lactic and glycolic acids, such as the Lupron Depot™ (injectable microspheres composed of polymers of lactic and glycolic acids and acetate leuprolide), and poly-D-(−)-3-hydroksibutil acid. While polymers such as ethylene vinyl acetate and the copolymer of lactic and glycolic acids, are capable of continuous release of molecules for over 100 days, certain hydrogels release proteins for shorter periods of time.

When the encapsulated polypeptide antagonists remain in the metabolism for a long time, they can denature or aggregate as a result of exposure to moisture at 37° C., which leads to loss of biological activity and possible changes in immunogenicity. In order to stabilize smart strategies can be worked out, depending on the current mechanism. For example, if the aggregation mechanism is found, that has the form of intermolecular S—S-connection through tiodisulfide exchange, stabilization can be achieved by modifying sulfhydrile residues, lyophilizing with the aim of removing acidic solutions, humidity control, using appropriate additives, and developing specific polymer matrix compositions.

Antagonistic compounds with a constant release of anti-FGFR1 agent also include antagonistic antibodies that are enclosed in liposomes. Liposomes containing the antagonist may be prepared by methods known in the field, for example, described by Epstein et al. (Proc. Nat. Acad. Sci. 82, 3688 (1985), Huang et al. (Rgoss. Nat. Acad. Sci. 77, 4030 (1980) U.S. Pat. No. 4,485,045 and U.S. Pat. No. 4,544,545.

Liposomes tend to have small size (of about 200-800 angstroms) and belong to a single-layer type in which the lipid content is higher than 30 mol. % cholesterol; the chosen ratio can be varied in order to select optimal conditions for therapy. Liposomes with long circulation are covered by U.S. Pat. No. 5,013,556.

Another way of using this invention is the incorporation of the antagonist of the FGF/FGFR1 path into products which have a definite shape. Such products can be used to modulate the growth of endothelial cells and angiogenesis. In addition, such products can be used to modulate tumor invasion and metastasis.

Conjugation of the FGF/FGFR1 path antagonist and of another preparation is possible. For prevention or treatment of a disease the required dose of antagonist will depend on the type of disease, on its severity and course, on whether the antibodies are introduced with preventive or therapeutic purposes, on the previous therapy, on the patient's anamnesis and his response to the antagonist, and on instructions from the attending physician. The antagonist may be administered to the patient in various ways, once or as a series of prescriptions.

FGF/FGFR1 antagonists can be used to treat various neoplastic and non-neoplastic diseases and disorders. Neoplasms and similar conditions that are amenable to such treatment, include renal cell cancer, lung cancer, stomach cancer, esophageal cancer, colorectal cancer, liver cancer, ovarian cancer, cervical cancer, endometrial cancer, endometrial hyperplasia, endometriosis, fibrosarcomas, horiosarkomas, tumors of the head and neck, hepatoblasts, Kaposi's sarcoma, melanoma, skin cancer, hemangioma, cavernous hemangioma, hemangioblastomas, pancreatic cancer, retinoblastoma, astrocytoma, glioblastoma, Schwan, oligodendroglioma, medulloblastoma, neuroblastoma, rabdomiosarkomu, osteogenic sarcoma, LMS, bladder cancer and other urothelial tumors, Wilms' tumor, prostate cancer, abnormal proliferation of blood vessels associated with phacomatoses.

The method can be used for non-neoplastic diseases that are treatable, including such as rheumatoid arthritis, psoriasis, atherosclerosis, diabetic retinopathy and other retinopathies, fibroplasia, neovascular glaucoma, thyroid hyperplasias (including Grave's disease), transplantation of the cornea and other tissues, chronic inflammations, lung inflammation, nephrotic syndrome, ascites, preeclampsia, pericardial effusion (for example, associated with pericarditis) and pleural effusion. Depending on the type of disease and its severity, the administration of the initial dose to a patient will range from 1 mg/kg to 15 mg/kg and can be administered by one or many individual injections or by continuous infusion. The usual daily dose may vary from about 1 mg/kg to 100 mg/kg or more, depending on the factors mentioned above. To re-introduce in a few days or more, depending on conditions, the treatment is repeated until a desired suppression of symptoms is achieved. But other modes of dosage can be used. The success of treatment can be easily determined by conventional methods and analyses, such as X-ray imaging of tumors.

In connection with another application of the invention, the efficiency of the FGF/FGFR1 path antagonist in preventing or treating disease may be improved by the introduction of the antagonist serially or in combination with another substance effective for this purpose, such as tumor necrosis factor, interferons, interleukins, antibodies and inhibitors able to neutralize or inhibit the angiogenic activity of endothelial growth factor of blood vessels and its receptors and/or hepatocyte growth factor and/or epidermal growth factor and its receptors and/or placental growth factor and/or mTOR and/or other intracellular kinases, or one or more of the conventional therapeutic agents such as, for instance, alkylating agents, folic acid antagonists, antimetabolites of nucleic acid metabolism, antibiotics, pyrimidine analogs, 5-flyuorouracil, purine nucleosides, amines, amino acids, triazole nucleosides, or corticosteroids. Such substances may be present in the composition administered, or can be administered separately. In addition, the FGF/FGFR1 path antagonist can be administered serially or in combination with radiological treatments, which may include both irradiation and introduction of radioactive substances.

In accordance with one of the applications of the invention in combined therapy tumor vascularization is under attack. One or more of the FGF/FGF.R1 antagonists are administered to the patient with a tumor in a therapeutically effective dose, defined, for example, in observing tumor necrosis or its metastatic foci, if any. This therapy continues for as long as there is no further improvement observed or a clinical examination shows that the tumor or its metastases have disappeared. With the progression of the disease one or more of the above substances is introduced, or hyperthermia, or radiation therapy.

Since the effectiveness of additional agents will vary, it is desirable to compare their effect on the tumor by standard screening matrix. The FGF/FGFR1 antagonist is re-administered as well as the additional agent, until you reach the desired clinical effect. Alternatively, the FGF/FGFR1 antagonist (s) are introduced together and, if desired, together with additional substances.

Use in Diagnostics

In diagnosis antibodies can be used to FGFR1 and also to his domains II and IIIc. The antibodies will generally be marked with residue, which is easy to detect. It can be any residue, which directly or indirectly, may produce a detectable signal. For example, it may be radioisotopes such as 3H, 14C, 32P, 35S, 125I; fluorescent or chemiluminescent compound, such as fluorescein isothiocyanate, rhodamine, or luciferin; tags marked with radioisotopes, such as, for example, 125I, 32P, 14C or 3H, or enzymes such as alkaline phosphatase betagalaktozidaza or horseradish peroxidase.

Any method known in the field can be used here for conjugation of the various antibodies to detectable residues, including the methods described by Hunter et al. (J Nature 144, 945 (1962), David et al. (J Biochemistry 13, 1014 (1974), Payne et al. (J. Immunol. Meth. 40, 219 (1981) and Nigren (J. Histochem. and Cytochem. 30, 407 (1982). The antibodies of this invention or FGF.R1 can be used in the diagnosis of tumors of humans and mammals. This means an antibody or FGFR1, marked with detectable residue, is introduced to a patient, preferably into the circulatory system, and the presence and location of the marked antibody or receptor in a patient's body is analyzed. Such visualization can be used, for example, in determining the stage of disease or the treatment of neoplasms. The antibody or FGFR1 are marked with any residue found in mammals, by known methods, such as nuclear magnetic resonance, radiology, etc. Below, as an example, some evidence is set down of these means of suppressing tumor growth (neutralizing) FGFR1, as well as of diagnosing the treating cancer and the suppression of tumor growth by blocking (neutralizing), as well as the method is presented as a way to diagnose cancer whose cells express FGFR1. The following examples are offered only as an illustration and should not be perceived as something to limit the present invention.

Example 1

(Results of KCRB-L03 Study): Analysis of Survival or Cell Proliferation In Vitro, Impaired Function of FGFR1 by Adding Monoclonal Antibodies, Blocking FGFR1 Domains II and IIIc FGFR1: To select a model of a cell line different cell lines were studied for hyperexpression of FGFR1:
1) The human renal cancer Caki-1
2) human breast cancer MCF7
3) human prostate cancer Du145
4) human non-small-cell lung cancer A549

Hyperexpression of FGFR1 on cells was determined in a standard Western blotting analysis. The highest overall level of expression of FGFR1 on cells was 40%. The highest level of expression of FGFR1 was detected on the cell line of human renal cancer Caki-1, the lowest—in the cells of the human prostate cancer Du145 (difference of 10): FIG. 3

Based on these data, a line of human renal cancer of Caki-1 was selected for further studies. Cells were seeded with a density of 104 cells/ml in 6-well plates. In each well there were added neutralizing monoclonal antibodies IO-1 and IO-2 in equal amounts but different concentrations. As control of part of the culture there were also added extraneous monoclonal antibodies without the neutralizing capacity (acquired in Abeam). After incubation, to each well was added FGF 2, up to 10 pg/ml. As an additional control, some cells were grown in the absence of both antibodies and FGF 2. After the growth of the culture for 3 weeks, the cells in each well were counted by a computer program on the analyzer of Hewlett Packard Scanjet (U.S.).

As shown in FIGS. 4 and 5, both monoclonal antibodies (IO-IO-1 and 2) completely inhibited the ability of added FGF 2 to support the growth and survival of renal cancer cell line (more than 90%). No significant differences in the activity of IO-IO-1 and 2 have been identified. A monoclonal antibody to FGFR1 without neutralizing capacity (Abcam) did not cause changes in cell survival. The experiment revealed that the suppression of mitogenic activity depends on the dose of the agent that blocks the FGF/FGFR1 path (the higher the dose, the higher mitogenic activity). The general conclusion of this example: while blocking domains II and IIIc FGFR1 achieved a strong inhibition of tumor cell growth.

Also, in this example we show that blocking the receptor of fibroblast growth factor leads to disruption of receptor autophosphorylation, which reflects its functional importance.

To this end, to the cells as described there were added antibody 10-1 and 1.5 hours later—FGF 2, 10 ng/ml. Cultivation took place for 5 minutes at a temperature of 37 C. Then the cells were washed and lysed in a special buffer for lysis (50 mM HEPES (pH 7.4), 150 mM NaCl, 10% glycerol, 1% Triton X-100, 1.5 mM MgCl2, protease inhibitors and 2 mmol of sodium vanadate.) Incubation of the lysate was carried out on ice for 30 minutes, and then it was centrifuged (13,000 rpm for 10 min at 4° C.). The concentration of protein in the lysate was measured in the analysis of Coomassie Plus (Pierce).

After that we conducted Immunoprecipitation/Western blotting. These techniques were performed by standard protocol (Santa Cruz Biotechnology, USA) using 1 mg of monoclonal antibody to bind to FGFR1 (control antibody; Santa Cruz Biotechnology), and anti-phosphotyrosine (4G10) antibodies. The resulting sample used for electrophoresis and subsequent identification of proteins in co-precipitated Western blotting. Some of the cells without the addition of FGF 2 and antibodies used for control. The resulting sample was used for electrophoresis and subsequent identification of co-precipitated proteins in Western blotting. Some of the cells without the addition of FGF 2 and antibodies were used as control.

Figure 6:
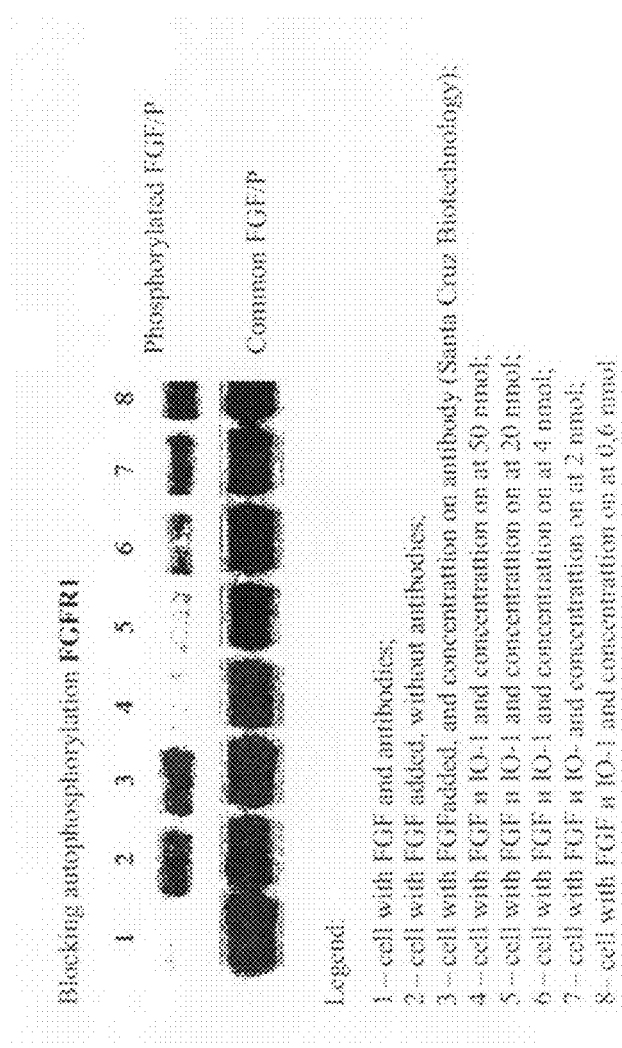

The results are shown in FIG. 6. It is shown that the monoclonal antibody 10-1 causes disturbance of phosphorylation of FGFR1, whereas the control antibody anti-FGFR1 (Santa Cruz Biotechnology, USA) did not prevent disruption of phosphorylation of receptor. Concentration of the blocking agent (in this case 10-1) affect the phosphorylation of FGFR1: the higher the concentration, the greater the effect. Thus, Example 1 (study of KCRB-L03) shows that cells in human renal cell cancer in the presence of FGF 2 proliferate, but when you block the target receptor FGFR1 (only domains II and IIIc) and disrupt its functions, they cease proliferating and lose their mitogenic activity. Moreover, in Example 1 it is demonstrated that the cells in the absence of FGF 2 do not proliferate either, and this is evidence of its mitogenic value (if FGF 2 is bound, the cells do not proliferate any longer).

Example 2

(Results of the Study of KCRB-L04): Analysis of Survival or Proliferation of Endothelial Cells In Vitro, Impaired Function of FGFR1 on Endothelial Cells after Adding a Monoclonal Antibody that Blocks the FGFR1

To analyze the survival of endothelial cells in the FGF medium and after blocking FGFR1 an experiment was conducted, similar to the blocking of vascular endothelial cells growth factor, as described in U.S. patent N 20,090,022,716 (Rockwell; Patricia et al. US Patent 20090022716). As a model of endothelial cells bovine capillary endothelium of the adrenal cortex was used (KEKN) (N. Ferrara et al. Proc. Nat. Acad. Sci. 84: 5773 (1987).

In the beginning, we found high expression of FGFR1 in the standard KEKN Western blotting analysis (FIG. 7).

Then KEKN were planted with a density of $5 \times 10^4$ cells/ml in 12 well plates. In each well was added 10 ng/ml FGF 2 in the presence or absence of various concentrations of monoclonal antibodies to FGF.R1, as well as an outsider without a monoclonal antibody neutralizing the activity of FGFR1 (Abcam). After the growth of the culture for 5 days the cells in each well were counted by a computer program for the analyzer Hewlett Packard Scanjet (U.S.). As an additional control KEKN was grown in the absence of FGF 2.

As shown in FIG. 8, both monoclonal antibodies to FGFR1 inhibited the ability of added FGF 2 to support the growth and survival of bovine KEKN. A monoclonal antibody with no neutralizing activity (Abeam) had no effect on cells.

Thus, Example 2 demonstrates that blocking the path FGF/FGFR1 endothelial cells cease to proliferate and lose their mitogenic activity, which can lead to disruption of angiogenesis in tumors.

Example 3

(Results of the Study KCRB-L05): Inhibition of Tumor Growth In Vivo by Blocking the FGF/FGFR1 Path Female mice (Beige/nude) aged 5-6 weeks (purchased from Harlan Sprague Dawley, Inc. (Indianapolis, USA) had introduced subcutaneously $2 \times 10^6$ tumor cells of the line of human renal cancer Caki-1 in 100 ml of physiological solution with phosphate buffer (FGFB). Once established tumor growth, mice were divided into 3 groups.

The first (treatment) group of mice was injected intraperitoneally 2 times a week, a monoclonal antibody IO-1 to FGFR1 in a dose of 100 mg/kg. The second (treatment) group of mice was injected intraperitoneally 2 times a week, a monoclonal antibody IO-2 FGFR1/heparan-sulfate, a dose of 100 mg/kg. Third (control) group of mice was injected with saline. Each group included 15 mice. The size of the tumor was measured every 5 days, and at the end of the study tumors were cut and weighed.

The effect of monoclonal antibodies/saline on the growth (volume) of tumors is shown in FIG. 9. The figure shows that those mice that had monoclonal antibodies introduced, blocking the FGFR1, tumor volume was significantly less than mice in the control group. Weight (median) of tumor control mice was significantly higher compared with mice treatment groups (p<0.001). The number of lung metastases was also significantly higher in control mice (p<0.01).

Those mice that received neutralizing monoclonal antibodies from the first week after inoculation, the cells Caki-1, the rate of tumor growth was significantly slower than in mice injected with saline.

Based on these data it was agreed that the method of suppressing tumor growth in vivo by blocking the FGF/FGFR1 path (through blocking of FGFR1 domains II and IIIc, is effective. Effect of monoclonal antibodies/saline growth upon the growth (volume) of tumors is shown in FIG. 9. The figure shows that in those mice that had monoclonal antibodies that block the FGFR1 introduced, tumor volume was significantly less than in mice of the control group. Tumor weight (median) of control mice was significantly higher compared to mice in treatment groups (p<0.001). The number of lung metastases was also significantly higher in control mice (p<0.01).

In those mice that received neutralizing monoclonal antibodies, starting from the first week after inoculation with the cells Caki-1, the rate of tumor growth was significantly slower than in mice injected with saline.

Based on these data, it was concluded that the method of suppressing tumor growth in vivo by blocking the FGF/FGFR1 path (through blocking of domains II and IIIc FGFR1) was effective.

Tables:

TABLE 1

Expression of FGFR1 in human renal cancer cells (primary tumor, metastases).

|  | N | FGFR1, % | FGFR1: nucleus, % | FGFR2, % | FGFR2: nucleus, % |
|---|---|---|---|---|---|
| RCC: primary tumor | 100 | 98 | 68 | 4 | — |
| RCC: metastases | 40 | 82.5 | — | 5 | — |
| Healthy individuals: Renal parenchyma | 40 | 2.5 | — | — | — |

Comparison with the expression of FGFR1 in renal parenchyma cells from healthy individuals and the expression of FGFR2 in human renal cancer cells (primary tumor, metastases).

TABLE 2

Concentration of FGF 1 and 2 in patients with metastatic renal cell cancer prior to medicinal treatment and in healthy volunteers

|  | Healthy individuals | Patients with metastatic RCC | P |
|---|---|---|---|
| FGF1, median, pg/ml | 1.7 | 4.8 | 0.03 |
| FGF2, median, pg/ml | 0.2 | 6.9 | <0.001 |

The invention claimed is:

1. A monoclonal antibody that is capable of simultaneously binding to domains II and IIIc of type 1 fibroblast growth factor receptor.

2. The monoclonal antibody according to claim 1 capable of inhibiting the mitogenic activity of the type 1 fibroblast growth factor receptor not less than 90%.

3. The monoclonal antibody according to claim 1 further including an amino acid sequence of the Fc domain of the heavy chain of one of the following: IgA, IgD, IgE, IgG1, IgG2, IgG3, IgG4, or IgM.

4. The monoclonal antibody according to claim 1 further including a human Fc domain.

5. The monoclonal antibody according to claim 4, further including the Fv domain of a mouse.

6. The monoclonal antibody according to claim 1 consisting of 100% human protein.

7. The monoclonal antibody according to claim 1 further including non-immunoglobulin polymer.

8. The monoclonal antibody according to claim 1 further including a cytotoxic part or amino acid sequence of a cytokine.

9. The monoclonal antibody according to claim 1 further including an Fc domain.

10. The monoclonal antibody according to claim 8, wherein the cytotoxic part is a polypeptide toxin.

11. The monoclonal antibody according to claim 10, wherein the cytotoxic part is capable of acting as an Fc-effector or capable of recruiting immunocompetent cells.

12. The monoclonal antibody according to claim 11, wherein the cytotoxic part is a polypeptide capable of binding a complement.

13. The antibody according to claim 1 further capable of binding to the human type 1 fibroblast growth factor receptor and being antagonistic to the interaction between the fibroblast growth factor and the type 1 fibroblast growth factor receptor.

* * * * *

SEQUENCE LISTING

<160> NUMBER OF SEQ ID NOS: 1

<210> SEQ ID NO 1
<211> LENGTH: 672
<212> TYPE: DNA
<213> ORGANISM: Homo sapiens

<400> SEQUENCE: 1

```
gataacacca aaccaaaccg tatgcccgta gctccatatt ggacatcccc agaaaagatg      60
gaaaagaaat tgcatgcagt gccggctgcc aagacagtga agttcaaatg cccttccagt     120
gggaccccaa accccacact gcgctggttg aaaaatggca agaattcaa acctgaccac      180 agaattggag gctacaaggt ccgttatgcc acctggagca tcataatgga ctctgtggtg     240
ccctctgaca agggcaacta cacctgcatt gtggagaatg agtacggcag catcaaccac     300
acataccagc tggatgtcgt ggagcggtcc cctcaccggc ccatcctgca agcagggttg     360
cccgccaaca agacagtggc cctgggtagc aacgtggagt tcatgtgtaa ggtgtacagt     420
gacccgcagc cgcatatcca gtggctaaag cacatcgagg tgaacgggag caagattggc     480
ccagacaacc tgccttatgt ccagatcctg aagactgctg gagttaatac caccgacaaa     540
gagatggagg tgcttcactt aagaaatgtc tcctttgagg acgcagggga gtatacgtgc     600
ttggcgggta actctatcgg actctcccat cactctgcat ggttgaccgt tctggaagcc     660
ctggaagaga gg                                                         672
```